(12) United States Patent
Bernstein

(10) Patent No.: US 11,166,925 B2
(45) Date of Patent: Nov. 9, 2021

(54) METHOD FOR ALLEVIATING KERATOCONJUNCTIVITIS SICCA

(71) Applicant: Elorac, Inc., Vernon Hills, IL (US)

(72) Inventor: Joel E. Bernstein, Highland Park, IL (US)

(73) Assignee: ELORAC, INC., Vernon Hills, IL (US)

( * ) Notice: Subject to any disclaimer, the term of this patent is extended or adjusted under 35 U.S.C. 154(b) by 0 days.

(21) Appl. No.: 16/110,369

(22) Filed: Aug. 23, 2018

(65) Prior Publication Data

US 2020/0061001 A1 Feb. 27, 2020

(51) Int. Cl.
*A61K 31/167* (2006.01)
*A61K 9/00* (2006.01)
*A61K 47/14* (2017.01)

(52) U.S. Cl.
CPC .......... *A61K 31/167* (2013.01); *A61K 9/0043* (2013.01); *A61K 47/14* (2013.01)

(58) Field of Classification Search
None
See application file for complete search history.

(56) References Cited

U.S. PATENT DOCUMENTS

| | | |
|---|---|---|
| 5,008,289 A | 4/1991 | Bernstein |
| 5,063,060 A | 11/1991 | Bernstein |
| 5,134,166 A | 7/1992 | Bernstein |
| 6,403,598 B1 | 6/2002 | Ueno et al. |
| 7,244,446 B2 | 7/2007 | Bernstein |
| 2007/0053957 A1* | 3/2007 | Kennedy ............ A61L 26/0004 424/443 |
| 2009/0093446 A1 | 4/2009 | Bernstein |
| 2016/0081968 A1 | 3/2016 | Svensson et al. |

FOREIGN PATENT DOCUMENTS

| | | |
|---|---|---|
| AR | 068669 A1 | 11/2009 |
| AU | 2007349197 A1 | 4/2009 |
| BR | PI0710595 A2 | 8/2011 |
| CA | 2644733 A1 | 4/2009 |
| CH | 690023 A5 | 3/2000 |
| CN | 101616663 A | 12/2009 |
| DE | 102004063363 A1 | 1/2006 |
| EP | 0646372 A | 4/1995 |
| EP | 2094256 A1 | 9/2009 |
| JP | 2009545634 A | 12/2009 |
| KR | 20090080017 A | 7/2009 |
| MX | 2008013039 A | 6/2009 |
| NZ | 571467 A | 3/2009 |
| WO | 2009045224 A1 | 4/2009 |
| WO | 2009087485 A2 | 7/2009 |

OTHER PUBLICATIONS

Kossena, A novel cubic phase of medium chain lipid origin for the delivery of poorly water soluble drugs, Journal of Controlled Release, 2004, 99, pp. 217-229. (Year: 2004).*
Kim, Capsaicin exhibits anti-inflammatory property by inhibiting IkB-a degradation in LPS-stimulated peritoneal macrophages, Cellular Signaling, 2003, 15, pp. 299-306 (Year: 2003).*
Patent Cooperation Treaty, "International Search Report and Written Opinion for PCT Patent Application No. PCT/US2018/047700", dated May 23, 2019, 7 pages.
European Patent Office, "Supplementary European Search Report for European Application No. 07868388.5", dated Oct. 8, 2009, 3 Pages.
European Patent Office, "Communication Pursuant to Article 94(3) EPC for European Application No. 07868388.5", dated Oct. 21, 2009, 4 Pages.
Opko Health, Incorporated, "Protocol OPK-03-201", Sep. 29, 2008, pp. 1-30.
European Patent Office, "Invitation Pursuant to Article 94(3) and Rule 71(1) EPC for European Application No. 07868388.5", dated Aug. 11, 2010, 2 Pages.
Patent Cooperation Treaty, "Written Opinion of the International Searching Authority for PCT Patent Application No. PCT/US07/80707", dated Aug. 21, 2008, 3 pages.
Patent Cooperation Treaty, "International Preliminary Report on Patentability for PCT Patent Application No. PCT/US07/80707", dated April 7, 2010, 4 pages.
Philip, et al., "The Human Nasal Response to Capsaicin", In J. Allergy Clin. Immunol, vol. 94, No. 6, Part 1, 1994, pp. 1035-1045.
Basquill, Sean M., "Non-Final Office Action For U.S. Appl. No. 11/868,286", dated May 28, 2010, 10 pages.
Basquill, Sean M., "Final Office Action For U.S. Appl. No. 11/868,286", dated Dec. 23, 2010, 8 pages.

* cited by examiner

*Primary Examiner* — Wu Cheng W Shen
*Assistant Examiner* — Andrew P Lee
(74) *Attorney, Agent, or Firm* — Medley, Behrens & Lewis, LLC

(57) ABSTRACT

Improved methods and compositions are disclosed for treating dry eye by administering intranasally a therapeutically effective amount of a capsaicinoid compound embedded in multiple layers of solid lamellar crystals of monoglycerides to patients with deficient tear production. The lipophilic capsaicinoid drug is embedded in multiple layers of solid lamellar crystals of monoglycerides, and these crystals are incorporated into pharmaceutically acceptable vehicles comprised of solutions, suspensions, foams, creams, ointments, and gels. The resulting formulations of the capsaicinoid are more stable, less irritating to skin and mucous membranes, and provide increased and more controlled release of the capsaicinoid compound.

10 Claims, No Drawings

METHOD FOR ALLEVIATING KERATOCONJUNCTIVITIS SICCA

FIELD

This disclosure relates to a method and compositions for alleviating keratoconjunctivitis sicca, a dry eye condition.

BACKGROUND

The condition of keratoconjunctivitis sicca or dry eye may affect as many as 9 million Americans over 50 years of age. Discomfort from dry eye ranges from a mild burning to a persistent sense of scratching under the lids. Dry eye is not just painful, but the condition can predispose to eye infections and also produce blurred vision. Dry eye is thought to be due to either an inability to produce sufficient tears or inflammation in the external eye.

Current attempts to treat dry eye focus on ophthalmic drops containing drugs to reduce inflammation in the eye. These drugs are cyclosporine and lifitegrast. However, both cyclosporine and lifitegrast drops frequently cause local irritation with burning and stinging, can blur vision, cause dysgeusia, reduce visual acuity and are poorly effective. There is consequently a substantial need for new therapies for dry eye which are more effective or which may produce less in the way of adverse ocular reactions.

In October 2007, applicant submitted a U.S. patent application Ser. No. 11/868,286, published as U.S. 2009/0093446, incorporated herein by reference, describing such a novel method (intranasal) of treating dry eye. However, the formulations of the capsaicinoid compounds utilized in this previously described (application Ser. No. 11/868,286) method proved to produce intolerable nasal irritation reactions in treated patients so that the prior invention could not be reduced to reasonable practice in a manner that made it operable for its intended purpose, and the application Ser. No. 11/868,286 was abandoned in 2010.

SUMMARY

Subsequent to this, applicant developed novel formulations of capsaicinoid nasal solutions, which, when administered intranasally, cause substantially less or no nasal irritation than the composition previously described or utilized and are well tolerated by patients. A second unanticipated advantage of these formulations is that they release the capsaicinoid compound over a longer duration and in increased amounts over a 24-hour period. In a recent clinical study in dry eye (Example 8), these formulations proved to be highly effective at increasing tear production and were well tolerated.

In developing an improved method for alleviating keratoconjunctivitis sicca, the present disclosure involves a very novel approach. It is focused on what is believed to be dysfunctional neural regulation of lacrimal gland secretion as an important element in the pathogenesis of keratoconjunctivitis sicca. Dry eye syndromes are diseases in which the quantity and composition of tears are altered, and these parameters are affected by defects in the neural activity of cranial nerves V (trigeminal) and VII (facial) which innervate the lacrimal gland. Terminal branches of the trigeminal and facial nerves are present in the nasal mucosa. Consequently, utilizing a nasal route of administration for compounds (capsaicinoids) known to affect the conductive functions of these nerves, readily and conveniently accesses the terminal branches of these nerves in the nasal mucosa. In doing so, the methods and formulations described herein provide a vastly improved method of increasing tear production without producing the adverse ocular effects (e.g. eye irritation, blurred or reduced vision) frequently produced by the installation of cyclosporine or lifitegrast drops into the eyes, as well as improves over the prior nasal treatment formulation as described above. Furthermore, by affecting the neural regulation of lacrimal gland secretion, this method produced more prompt improvement in patient's eyes then the slower anti-inflammatory actions of the current therapies.

An improved method and compositions for increasing tear production comprises intranasally administering a therapeutically effective amount of a capsaicinoid compound embedded in multiple layers of solid lamellar crystals of monoglycerides, to patients with deficient tear production. It was surprising and unexpected to use a nasal route of administration to successfully treat an ocular condition. To the inventor's knowledge, no nasal preparations have been reported to successfully treat disorders of the eyes while minimizing ocular irritation.

A method of treating keratoconjunctivitis sicca, also known as dry eye, includes administration of an effective amount of a composition containing lipoidal microencapsulated capsaicinoid compounds to the nasal mucosa with a resulting significant increase in production of ocular tearing without the localized ocular burning, stinging, blurring of vision and other adverse symptoms and signs attendant to the use of current treatments for dry eye.

A suitable capsaicinoid compound, for example, includes capsaicin, civamide, acetylated derivatives of capsaicin and civamide, or salts of all of the aforementioned capsaicinoids.

Compositions disclosed herein are comprised of the above referenced capsaicinoid compounds in concentrations of about 0.001 to about 5.0% by weight microencapsulated within solid crystals of monoglycerides and incorporated into vehicles suitable for nasal administration. Use of such compositions results in markedly diminished nasal irritation as compared to compositions cited in U.S. application Ser. No. 11/868,286, and also provide for a more prolonged and quantitatively greater release of the active capsaicinoid over a 24-hour period.

The topical formulations are comprised of the monoglyceride encapsulated capsaicinoids incorporated into a vehicle suitable for administration to the nasal mucosa such as solutions, suspensions, creams, ointments, gels or foams.

DETAILED DESCRIPTION

The inventor has surprisingly discovered an improved method of producing increased tear production (lacrimation) without the adverse intraocular side effects noted with the eye drops currently utilized to treat patients with dry eye and without the undesirable nasal irritation elicited by the compositions disclosed in U.S. application Ser. No. 11/868,286. This method consists of the intranasal administration of a class of chemicals called capsaicinoids encapsulated in lipoidal microcapsules, resulting in increased tear production without significant irritation to the eyes and intranasal cavities themselves.

Suitable capsaicinoid compounds for the formulation described herein include, for example, capsaicin, civamide, acetylated derivatives of capsaicin and civamide, or salts of all of the aforementioned capsaicinoids. Among the safest and most effective capsaicinoid utilized in this new method is civamide (cis-8-methyl-N-vanillyle-nonenamide), a chemical that has been the subject of two previous U.S.

Patents (U.S. Pat. Nos. 5,063,060 and 7,244,446) incorporated here by reference. In the course of conducting a number of clinical investigations utilizing intranasal capsaicinoids for treatment of headache and neuralgia pain, as well as nasal stuffiness, it was discovered surprisingly that intranasally administered capsaicinoids produce increased ocular tear production without undesirable effects on the eyes.

This surprising finding was set forth in U.S. application Ser. No. 11/868,286. However, the capsaicinoid compositions utilized and referred to in that Application produced intense initial pain, burning and stinging in the nasal mucosa, causing the vast majority of patients to immediately discontinue this therapy before they could realize any benefit.

To try to surmount this problem and make capsaicinoid compositions less irritating to the nasal mucosa, and thus more tolerable, U.S. application Ser. No. 11/868,286 provided for incorporation into the compositions of either a local anesthetic or topically effective corticosteroid. The inventor nevertheless discovered after filing Ser. No. 11/868,286 that while incorporation of a local anesthetic or topical steroid might minimally ameliorate the adverse effects of the capsaicinoid on the nasal mucosa, the resulting formulations were still too irritating for most subjects to tolerate.

The inventor subsequently investigated several different approaches to reduce the irritancy of these capsaicinoid containing formulations. Only one of these approaches was successful and it is in part the subject of this Application.

In an embodiment, the active compound is encapsulated in a solid crystal of a monoglyceride. This enables the compound to be effectively used as an acceptable treatment for keratoconjunctivitis avoiding significant irritation of the prior formulation. Monoglycerides are a class of glycerides including a molecule of glycerol linked with an ester bonded to a fatty acid. A fatty acid has a 4 to 28 carbon atom chain, such as 6 to 21, or 10 to 15 carbon atoms. The carbon atom chain may be straight or branched and saturated or unsaturated. While a variety of glycerides of short to medium chain fatty acids can be used to encapsulate the capsaicinoid compound, 1-glyceryl monolaurate and 1-glyceryl monomyristate are the preferred monoglycerides for the composition disclosed herein. When the fatty acid is attached to a primary alcohol, the resultant compound is a 1-monoglyceride and when attached to a secondary alcohol, the compound is designated a 2-monoglyceride. In an embodiment, the monoglyceride has a melting point of about 25° C. to about 65° C., such as about 30° C. to about 45° C., or about 32° C. to about 35° C. In an embodiment, two or more monoglycerides are used in the composition.

In an embodiment, the monoglyceride is a polar lipid that is in a lamellar, crystalline phase. Monoglycerides are widely used in foods as emulsifiers to prevent mixtures of oils and water from separating. They are also incorporated in some cosmetics to enhance skin hydration and barrier function. However, by heating a batch of certain active pharmaceutical ingredients (APIs), e.g., the capsaicinoid compounds described herein with a monoglyceride and water until the monoglyceride is dissolved (e.g., to about 60° C. to about 100° C., or about 65° C. to about 80° C.), stirring for about 15 to about 20 minutes under an inert nitrogen atmosphere ("nitrogen blanket"), then cooling the mixture to cause crystallization of the monoglyceride, individual molecules of the API can be coated with an envelope of monoglyceride particles. These particulate monoglyceride shells can be hydrolyzed in the skin or mucosa membranes to release glycerin and fatty acids and in doing such, also release the API.

In the pre-mixed and pre-heated composition, the monoglycerides may be added in an amount of about 10 to about 50% by weight, such as about 15% to about 35%, or about 25% to about 30% by weight. Water may be present in an amount of 50% to 90%, such as about 60% to about 80%, or about 65% to about 75%. The APIs and other inactive ingredients may be added in an amount of about 0.001% to about 10%, such as about 0.1% to about 7%, or about 1% to about 5%. The monoglyceride may be in a weight ratio with the capsaicinoid compound of about 10,000:1 to about 30:1, such as, for example, about 5000:1 to about 100:1, or about 3000:1 to about 300:1.

In accordance with the present disclosure, about 0.001% to about 5.0% by weight of the total composition, such as, for example, about 0.01% to about 1%, or about 0.015% to about 0.5%, of capsaicin, civamide, acetylated derivatives or salts of capsaicin and civamide are embedded in multiple layers of solid lamellar crystals of monoglycerides from 40-100 Å thick, such as 50 to 90 Å, or 60 to 80 Å, and incorporated into formulations such as solutions, suspensions, lotions, creams, gels, ointments and foams and then introduced into the nasal passages.

The formulation can, for example, be introduced into the nasal passages by a drop or spray of a solution or suspension of the capsaicinoid compound. The patients generally administer the formulation utilized into the left, right or both nasal passages once or twice daily.

Other pharmaceutically acceptable excipient components suitable for an intranasally delivered formulation for mammals may be added to the composition. These may include, for example, preservatives and emulsifiers, for example, polyoxyethylene(20) oleyl ether (BRIJ-98) and polyethylene glycol stearate (Myrj 59).

The above described compositions and method produces effective stimulus of increased tear production without untoward ocular side effects such as stinging or blurred vision in the eyes and intranasal irritation. The compositions described herein reduce the frequency and/or severity of intranasal side effects by incorporating the capsaicinoid compound into lipoidal microspheres which provide a prolonged and more substantial release of the capsaicinoid on the nasal mucosa.

EXAMPLES

Examples are provided for illustrative purposes and are not intended to limit the scope of the disclosure.

Example 1

Thirty (30) normal volunteers divided into 3 separate 10 subject panels participated in a multi-dose, 14 day tolerance study evaluating the local effects of civamide nasal spray composed of ethyl alcohol; polysorbate 20; potassium phosphate monobasic; EDTA disodium; sodium phosphate dibasic dehydrate; benzalkonium chloride; butylated hydroxytoluene; and purified water with varying amounts of civamide. To the first 10 subject panel, the nasal spray formulation was administered twice daily, and the civamide was 0.0075% by weight. The second 10 subject panel was administered the same formulation but with 0.01% by weight civamide administered twice daily; and the third 10 subject panel was administered the same formulation but with 0.015% by weight civamide administered once daily. Ten (10) of 10 (100%) of the subjects in each of the two groups receiving civamide twice daily related that they experienced increased lacrimation (tear production), while 9 of 10 (90%) of subjects utilizing 0.015% by weight civamide once daily experienced increased tearing.

Example 2

Fifty-five (55) patients with vasomotor rhinitis (non-allergic rhinitis) participated in a double-blind placebo-controlled 2 week evaluation of the symptomatic relief afforded patients by 0.01% by weight civamide nasal spray or placebo nasal spray (vehicle for active product). Thirty-one percent (31%) of patients using 0.01% civamide spray reported increased tearing, while 0% of patients on placebo noted such a side effect.

Example 3

Thirty-four (34) patients with migraine headache applied 0.025% by weight capsaicin cream to their nasal mucosa for relief of their headache. Seventy-three percent (73%) of such patients noted some relief of their headaches 4 hours after administration of 0.025% capsaicin cream. Forty-four percent (44%) of these patients reported increased tearing as a side effect.

Example 4

In a study utilizing 0.025% by weight civamide nasal drops administered once daily for 1 week to 28 patients with episodic cluster headache (a severe form of vasomotor headache that occurs in general 4-24 week clusters), 9 of 18 patients (50%) on civamide nasal drops had increased tearing versus 0 of 10 patients (0%) on vehicle control.

Example 5

In 112 episodic cluster headache patients administered either 0.01% by weight civamide nasal spray or inactive control (10% NaCl) twice daily, 36 patients (51%) on civamide spray and 3 patients (7%) on control reported increased tearing.

Example 6

Two patients with migraine headache disorder were administered 0.025% by weight capsaicin cream intranasally for acute relief of their migraine pain. Both reported lacrimation within 30 minutes of application of the capsaicin cream.

Example 7

Five batches of microencapsulated civamide in accordance with the technology described herein were prepared as follows:

TABLE 1

Compositions of Microencapsulated Civamide

| Chemical Composition (wt %) | Batch 1 | Batch 2 | Batch 3 | Batch 4 | Batch 5 |
|---|---|---|---|---|---|
| 1-glyceryl monolaurate | 7 | 7 | 7 | 7 | 7 |
| 1-glyceryl monomyristate | 21 | 21 | 21 | 21 | 21 |
| Civamide | 0.01 | 0.025 | 0.075 | 0.075 | 0.10 |
| Myrj 59 | 0 | 0 | 1 | 0 | 1 |
| Brij 98 | 0 | 0 | 0 | 2 | 1 |
| RO-water | 72 | 71.9 | 70.9 | 69.9 | 69.9 |

Batches were manufactured in a lab-scale reactor in a nitrogen atmosphere with heating to 70° C. provided by a water bath. Components were stirred at the elevated temperature for 15 minutes and then cooled to room temperature. At about 33-36° C. crystallization of the monoglycerides to encapsulate the civamide takes place.

The microencapsulated civamide was then added to solutions, creams, suspensions, ointments, gels and foams.

Example 8

Twenty-five (25) patients with keratoconjunctivitis sicca utilized a 0.01% microencapsulated civamide solution (Batch 1 from Example 7) as a nasal spray self-administered twice daily for 12 weeks. The patients were evaluated for tear production and disease symptomology with a Schirmer Test and Ocular Surface Disease Index (OSDI) respectively. Eighteen (18) of the 25 improved markedly (72%) on the Schirmer test by the end of the study, and 24 of the 25 patients (96%) were improved on the OSDI by study's end. None reported any significant nasal irritation.

Example 9

To evaluate the release of the capsaicinoid from the monoglycerol microencapsulated formulations (this Application) versus the non-encapsulated formulations (U.S. application Ser. No. 11/868,286), a Franz diffusion cell system was utilized to compare API release from a batch of 0.075% civamide encapsulated by monoglycerol (Batch 3 from Example 7) to a batch of non-encapsulated civamide cream (commercial Zuacta® cream) in identical vehicles composed of benzyl alcohol, cetyl alcohol, glyceryl stearate, isopropyl myristate, PEG-100 stearate, purified water, sorbitol solution and white petrolatum. The comparative API (civamide) release at 2, 6 and 24 hours is provided in Table 2 below. As can be observed in Table 2, the monoglyceride encapsulated formulation released more than 4 times the amount of civamide over 24 hours than did the non-encapsulated formulation.

TABLE 2

| Batch | Time (h) | Total Amount of Civamide Release ($\mu g/cm^2$) |
|---|---|---|
| .075 civamide encapsulated | 2 | 8.1 |
| .075 civamide non-encapsulated | 2 | 0.5 |
| .075 civamide encapsulated | 6 | 16.8 |
| .075 civamide non-encapsulated | 6 | 3.9 |
| .075 civamide encapsulated | 24 | 42.7 |
| .075 civamide non-encapsulated | 24 | 9.8 |

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in the same manner as the term "comprising," as "comprising" is interpreted when employed as a transitional word in a claim. The term "consisting essentially" as used herein means the specified materials or steps and those that do not materially affect the basic and novel characteristics of the material or method. All percentages and averages are by weight unless the context indicates otherwise. If not specified above, properties mentioned herein may be determined by applicable ASTM standards, or if an ASTM standard does not exist for the property, the most commonly used standard known by those of skill in the art may be used. The articles "a," "an," and "the," should be interpreted to mean "one or more" unless the context indicates the contrary.

It is claimed:

1. A method of treating keratoconjunctivitis sicca comprising:
   intranasally administering to the nasal mucosa an effective amount of a composition comprising a capsaicinoid compound embedded in lamellar crystals of a monoglyceride and in a vehicle suitable for intranasal administration;
   wherein the capsaicinoid compound is present in the composition in a range of about 0.001% by weight to about 1% by weight,
   wherein the composition does not cause nasal irritation.

2. The method of claim 1, wherein said capsaicinoid compound is selected from the group consisting of capsaicin, civamide, acetylated derivatives of capsaicin and civamide, and pharmaceutically acceptable salts of the above.

3. The method of claim 1, wherein the capsaicinoid compound is present in the composition in a range of about 0.01% by weight to about 0.50% by weight.

4. The method of claim 2, wherein the capsaicinoid compound is present in the composition in a range of about 0.01% by weight to about 0.50% by weight.

5. The method of claim 1, wherein the vehicle is selected from the group consisting of solutions, suspensions, creams, ointments, gels and foams.

6. The method of claim 1, wherein the monoglyceride comprises a fatty acid with a 4 to 28 carbon atom chain.

7. The method of claim 1, wherein the monoglyceride has a melting point of about 25° C. to about 65° C.

8. The method of claim 1, wherein the composition comprises two or more monoglycerides.

9. The method of claim 1, wherein the monoglyceride is selected from the group consisting of: 1-glyceryl monolaurate, 1-glyceryl monomyristate, and combinations thereof.

10. The method of claim 6, wherein the fatty acid is a saturated fatty acid.

* * * * *